United States Patent [19]
Schmidhammer et al.

[11] Patent Number: 5,994,327
[45] Date of Patent: Nov. 30, 1999

[54] PROCESS FOR THE PREPARATION OF MORPHINANS

[75] Inventors: Helmut Schmidhammer, Innsbruck; Peter Schwarz, Brandenberg, both of Austria; Zhong-Yong Wei, Pierrefonds, Canada

[73] Assignee: Astra AB, Sweden

[21] Appl. No.: 08/809,307

[22] PCT Filed: Nov. 11, 1996

[86] PCT No.: PCT/SE96/01497

§ 371 Date: Mar. 13, 1997

§ 102(e) Date: Mar. 13, 1997

[87] PCT Pub. No.: WO98/22467

PCT Pub. Date: May 28, 1998

[30] Foreign Application Priority Data

Nov. 17, 1995 [SE] Sweden ................... 9504114

[51] Int. Cl.$^6$ ........... A61K 31/695; A61K 31/44; C07D 491/12; C07F 7/02
[52] U.S. Cl. ............. 514/63; 514/279; 546/14; 546/35
[58] Field of Search ........... 546/14, 35; 514/63, 514/279

[56] References Cited

U.S. PATENT DOCUMENTS

| | | | |
|---|---|---|---|
| 4,816,586 | 3/1989 | Portoghese | 544/340 |
| 5,223,507 | 6/1993 | Dappen et al. | 514/279 |
| 5,225,417 | 7/1993 | Dappen et al. | 514/279 |
| 5,332,818 | 7/1994 | Nagase et al. | 546/37 |
| 5,354,863 | 10/1994 | Dappen et al. | 546/35 |
| 5,436,249 | 7/1995 | Dappen et al. | 514/279 |

FOREIGN PATENT DOCUMENTS

| | | |
|---|---|---|
| 614 898 | 9/1994 | European Pat. Off. . |
| 456 833 | 3/1995 | European Pat. Off. . |
| 485 636 | 3/1997 | European Pat. Off. . |
| 3412727 | 4/1984 | Germany . |
| 95/31463 | 11/1995 | WIPO . |

OTHER PUBLICATIONS

Arakawa, et al., "Immunosuppression by Delta Opioid Receptor Antagonist," *Transplant.Proc.* 25:738–740 (1993).

Arakawa, et al., "Immunosuppressive Effect of δ–Opioid Receptor Antagonist on Xenogeneic Mixed Lymphocyte Reaction," *Transplant. Proc.* 24:696–697 (1992).

Arakawa, et al., "The Immunosuppresive Effect of δ–Opioid Receptor Antagonist on Rat Renal Allograft Survival," *Transplantation* 53:951–953 (1992).

Chem. Abstr. vol. 122, , pp. 1086–1087, abstr. #187841c, "Synthesis of N1'–([$^{11}$C]methyl)naltrindole . . . " (1995).

Portoghese, "An Approach to the Design of Receptor–Type–Selective Non–Peptide Antagonists of Peptidergic Receptors: δ Opioid Antagonists," *J. Med. Chem.* 34:1757–1762 (1991).

*Primary Examiner*—Alan L. Rotman
*Attorney, Agent, or Firm*—Michael A. Sanzo; Vinson & Elkins L.L.P.

[57] ABSTRACT

A process for the preparation of 14-alkoxyindolomorphinans and 14-alkoxybenzofuranomorphinans is disclosed. The process facilitates the preparation of a large variety of 14-alkoxy substituted indolomorphinans and benzofuranomorphinans in which a 3-hydroxy substituent is present.

28 Claims, No Drawings

PROCESS FOR THE PREPARATION OF MORPHINANS

CROSS-REFERENCE

This application is a S371 of PCT/SE96/01497 filed Nov. 19, 1996.

FIELD OF THE INVENTION

The present invention is directed to a new process for the preparation of 14-alkoxyindolomorphinans and 14-alkoxybenzofuranomorphinans.

BACKGROUND OF THE INVENTION

Opioid antagonists have been indispensable as tools in opioid research. For example, the chief criterion for the classification of an agonist effect as being opioid receptor mediated is the ability of known opioid antagonists naloxone or naltrexone to reversibly antagonize this effect in a competitive fashion. The usefulness of naloxone and naltrexone for this purpose stems from the fact that they are universal opioid antagonists; that is, they are capable of antagonizing the agonist effects mediated by multiple opioid receptor types.

In addition to their uses as pharmacological tools, selective, non-peptide opioid antagonists have been described as having potential clinical applications in the treatment of a variety of disorders where endogenous opioids play a modulatory role. These include for instance disorders of food intake, shock, constipation, mental disorders, CNS injury, alcoholism, and immune function (P. S. Portoghese at al., J. Med. Chem., Vol. 34: 1757–1762, 1991).

Non-peptide, competitive, δ-selective opioid antagonists have been found to have immunosuppressive potency and less toxicity than the presently used immunosuppressive compound cyclosporin (EP 456 833; EP 485 636; EP 614 898; K. Arakawa et al., Transplantation, Vol. 53: 951–953, 1992; K. Arakawa et al., Transplant Proc., Vol. 24: 696–697, 1992; K. Arakawa et al., Transplant Proc., Vol. 25: 738–740, 1993). Such immunosuppressive agents can be used after organ transplantation to suppress the rejection of the foreign organ and also in the treatment of autoimmune diseases (e.g. rheumatoid arthritis).

In U.S. Pat. No. 5,223,507 and U.S. Pat. No. 5,225,417 the synthesis of 14-O-substituted indolomorphinans and benzofuranomorphinans have been disclosed. According to the process used for preparing the compounds claimed and disclosed in U.S. Pat. No. 5,223,507, only a 3,14-dimethoxy substituted benzofuranomorphinan was prepared. According to the process used for preparing compounds claimed and disclosed in U.S. Pat. No. 5,225,417, two 14-O-alkyl substituted benzofuranomorphinans have been prepared. According to the methods used for preparing the compounds of both the two mentioned prior art documents, the 3-hydroxy group was protected by a methyl group which is not easily removed without having a loss in yield.

According to the processes known from the prior art, the variations of the substituents at the oxygen in position 14 are very much limited when a 3-hydroxy group is supposed to be present in the molecule. It is for instance not possible to prepare compounds with a substituent at the oxygen in 14-position, as this position is labile to the conditions used for the cleavage of the 3-methoxy group.

Thus, the object of the present invention was to find a new process which would facilitate the preparation of 14-O-substituted indolomorphinans and benzofuranomorphinans.

The present patent application discloses a process whereby naloxone, naltrexone or oxymorphone is used as the starting material, whereby the 14-alkoxy group is introduced after the protection of the oxygen in 3-position with an easily removable protecting group, preferably benzyl, methoxymethyl, ethoxymethyl, trityl or silyl, thereby providing a process enabling the synthesis of compounds involving 14-O-substitution.

OUTLINE OF THE INVENTION

The present invention is directed to a new process for the preparation of compounds of the general formula (I)

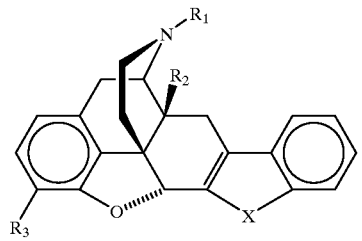

(I)

wherein $R_1$ represents allyl, cyclopropylmethyl or methyl;

$R_2$ represents $C_1$–$C_6$ alkoxy, $C_1$–$C_6$ alkenyloxy, $C_7$–$C_{16}$ arylalkyloxy wherein aryl is $C_6$–$C_{10}$ aryl and alkyloxy is $C_1$–$C_6$ alkyloxy, $C_7$–$C_{16}$ arylalkenyloxy wherein aryl is $C_6$–$C_{10}$ aryl and alkenyloxy is $C_1$–$C_6$ alkenyloxy, $C_1$–$C_6$ alkanoyloxy, $C_7$–$C_{16}$ arylalkanoyloxy wherein aryl is $C_6$–$C_{10}$ aryl and alkanoyloxy is $C_1$–$C_6$ alkanoyloxy;

$R_3$ represents hydroxy, $C_1$–$C_6$ alkoxy, $C_7$–$C_{16}$ arylalkyloxy wherein aryl is $C_6$–$C_{10}$ aryl and alkyloxy is $C_1$–$C_6$ alkyloxy, $C_1$–$C_6$ alkenyloxy, $C_1$–$C_6$ alkanoyloxy, $C_7$–$C_{16}$ arylalkanoyloxy wherein the aryl is $C_6$–$C_{10}$ aryl and the alkanoyloxy is $C_1$–$C_6$ alkanoyloxy, $C_2$–$C_{10}$ alkyloxyalkoxy wherein alkyloxy is $C_1$–$C_4$ alkyloxy and alkoxy is $C_1$–$C_6$ alkoxy; and X represents O, NH or $NR_4$ wherein $R_4$ is $C_1$–$C_6$ alkoxy, $C_1$–$C_6$ alkenyloxy, $C_7$–$C_{16}$ arylalkyloxy wherein aryl is $C_6$–$C_{10}$ aryl and alkyloxy is $C_1$–$C_6$ alkyloxy, $C_7$–$C_{16}$ arylalkenyloxy wherein the aryl is $C_6$–$C_{10}$ aryl and alkenyloxy is $C_1$–$C_6$ alkenyloxy, $C_1$–$C_6$ alkanoyloxy, $C_7$–$C_{16}$ arylalkanoyloxy wherein aryl is $C_6$–$C_{10}$ aryl and alkanoyloxy is $C_1$–$C_6$ alkanoyloxy.

The process for the preparation of the compounds of the general formula (I) comprises the following steps:

(i) Naloxone (II), naltrexone (III) or oxymorphone (IIIa) of the formula

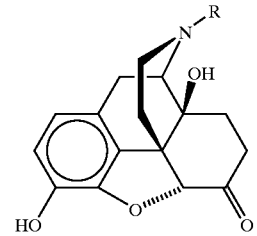

(II): R = allyl
(III): R = cyclopropylmethyl
(IIIa): R = methyl is reacted with phenylhydrazine hydrochloride in the presence of an acid, preferably methanesulfonic acid, sulfuric acid or hydrochloric acid, giving naloxindole (NLI), naltrindole (NTI) or oxymorphindole (OMI), P S. Portoghese et al., J. Med. Chem. Vol. 31: 281–282, 1988, of the following formula:

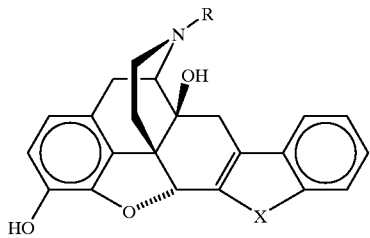

NLI: R = allyl, X = NH
NTI: R = cyclopropylmethyl, X = NH
OMI: R = methyl, X = NH or;

naloxone (IT), naltrexone(III) or oxymorphone is reacted with O-phenyl-hydroxyl amine hydrochloride in the presence of an acid, preferably methanesulfonic acid, sulfuric acid or hydrochloric acid, giving the benzofurane derivatives NLB, naltriben (NTB; P. S. Portoghese et al., J. Med. Chem., Vol. 34: 1715–1720, 1991) or OMB (U.S. Pat. No. 5,223,507) of the formula

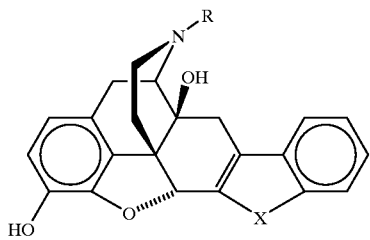

NLB: R = allyl, X = O
NTB: R = cyclopropylmethyl, X = O
OMB: R = methyl, X = O (ii) the 3-hydroxy group is protected by alkylation with benzyl bromide, methoxymethyl bromide, ethoxymethyl bromide, trityl chloride or a silylating agent, preferably dimethyl isobutyl-silyl chloride, trimethylsilyl chloride, triethylsilyl chloride, t-butyldimethylsilyl chloride or tri-i-propylsilyl chloride, in a solvent, preferably N,N-dimethylformamide, dichloromethane or tetrahydrofurane, in the presence of a base which may not be a weak base, preferably potassium carbonate, potassium hydroxide, sodium hydride, sodium amide or diisopropyl ethylamine, giving a compound of the formula (IV)

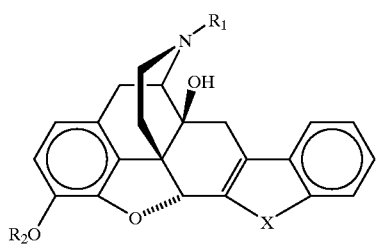

wherein
$R_1$ is allyl, cyclopropylmethyl or methyl;

$R_2$ is benzyl, methoxymethyl, ethoxymethyl, trityl or silyl, preferably dimethyl isobutyl silyl, trimethylsilyl, triethylsilyl, t-butyldimethylsilyl or tri-i-propylsilyl; and X is NH, O, N-benzyl, N-methoxymethyl, N-ethoxymethyl, N-trityl or N-silyl, preferably dimethyl isobutyl silyl, trimethylsilyl, triethylsilyl, t-butyldimethylsilyl or tri-i-propylsilyl;

(iii) the compound of the formula (1V) is treated with $C_1$–$C_2$ dialkyl sulfates, $C_1$–$C_6$ alkyl halides, $C_1$–$C_6$ alkenyl halides, $C_7$–$C_{16}$ aralkyl halides wherein the aryl is $C_6$–$C_{10}$ aryl and the alkyl is $C_1$–$C_6$ alkyl, $C_7$–$C_{16}$ arylalkenyl halides wherein the aryl is $C_6$–$C_{10}$ aryl and the alkenyl is $C_2$–$C_6$ alkenyl, $C_2$–$C_6$ alkanoyl halides, $C_7$–$C_{16}$ arylalkanoyl halides wherein the aryl is $C_6$–$C_{10}$ aryl and the alkanoyl is $C_2$–$C_6$ alkanoyl, in a solvent, preferably N,N-dimethyl formamide or tetrahydrofurane, using a strong base, preferably sodium hydride, potassium hydride or sodium amide, giving a compound of the formula (V)

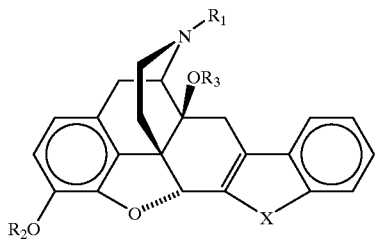

wherein $R_1$ is allyl or cyclopropylmethyl;

$R_2$ is benzyl, methoxymethyl, ethoxymethyl, trityl or silyl, preferably dimethyl isobutyl silyl, trimethylsilyl, triethylsilyl, t-butyldimethylsilyl or tri-i-propylsilyl; and $R_3$ is $C_1$–$C_6$ alkyl, $C_1$–$C_6$ alkenyl; $C_7$–$C_{16}$ arylalkyl wherein the aryl is $C_6$–$C_{10}$ aryl and the alkyl is $C_1$–$C_6$ alkyl; $C_7$–$C_{16}$ arylalkenyl wherein the aryl $C_6$–$C_{10}$ aryl and the alkenyl is $C_1$–$C_6$ alkenyl; $C_1$–$C_6$ alkanoyl, $C_7$–$C_{16}$ arylalkanoyl wherein the aryl is $C_6$–$C_{10}$ aryl and the alkyl is $C_1$–$C_6$ alkyl;

X is as defined in the formula (IV) above; and optionally the following step (iv) whereby (iv) the compound of the formula (V) wherein X is NH, O, N-benzyl, N-methoxymethyl, N-ethoxymethyl, N-trityl or silyl, preferably dimethyl isobutyl silyl, trimethylsilyl, triethylsilyl, t-butyldimethylsilyl or tri-i-propylsilyl;

is hydrolized in diluted acids, preferably hydrochloric acid or sulfuric acid, optionally in the presence of a solvent, preferably an alcohol, and in particular methanol, ethanol or n-propanol, giving a compound of the formula (VI)

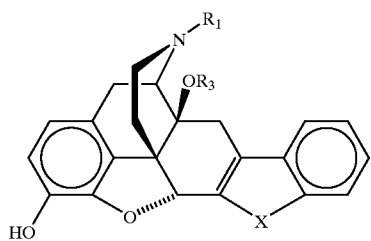

(VI)

wherein $R_1$, and $R_3$ are as defined above in formula (V), and X is NH, O or N-benzyl; and (v) the compound of the formula (VI) is alkylated or acylated, giving a compound of the formula (1).

DETAILED DESCRIPTION OF THE INVENTION

The invention will now be described in more detail by the following examples.

EXAMPLES

Example 1

Synthesis of 17-(Cyclopropylmethyl)-6,7-dehydro-4,5α-epoxy-14-hydroxy-3-(methoxymethoxy)-6,7-2',3'-benzo[b]furanomorphinan (compound 1). Sodium hydride (426 mg, 17.7 mmol; obtained from 710 mg of sodium hydride dispersion in oil by washings with n-hexane) was added to a solution of naltriben methanesulfonate (2.0 g, 3.9 mmol) in 30 ml of anhydrous N,N-dimethyl formamide at 0° C. The resulting mixture was stirred at 0° C. for 20 min and then at room temperature for another 60 min. After cooling to 0° C., methoxymethyl bromide (653 μl, 8 mmol) was added and stirring was continued for 15 min at 0° C. and then for additional 120 min at room temperature. Excess sodium hydride was destroyed by addition of methanol and $H_2O$. The resulting mixture was extracted with ethyl acetate (4×50 ml), the combined organic layers were washed with $H_2O$ (2×50 ml) and brine, dried over $Na_2SO_4$ and evaporated to give an oil which was crystallized from MeOH to yield 1.0 g (56%) of compound 1. M. p. 129–130° C.

$^1$H-NMR ($CDCl_3$): δ 7.45 (d, J=8.3 Hz, 1 arom. H), 7.37 (d, J=8.3 Hz, 1 arom. H), 7.25 (m, 1 arom.H), 7.16 (m, 1 arom.), 6.86 (d, J=8.3 Hz, 1 arom. H), 6.60 (d, J=8.3 Hz, 1 arom. H), 5.63 (s, H—C(5)), 5.17 and 5.06 (2 d, J=6.6, 6.6 Hz, $OCH_2O$), 3.42 (s, $CH_3O$). Analysis calculated for $C_{28}H_{29}NO_5$. 0.2 MeOH (465.95): C 72.69, H 6.45, N 3.01; found: 72.58, H 6.28, N 3.00.

Example 2

Synthesis of 17-(Cyclopropylmethyl)-6,7-dehydro-4,5α-epoxy-14-hydroxy-3-(methoxymethoxy)-6,7-2',3'-(N-methoxymethylindolo)morphinan (compound 2).

Sodium hydride (492 mg, 20.5 mmol; obtained from 820 mg of 60% dispersion in oil by washings with n-hexane) was added to a solution of naltrindole hydrochloride (1.5 g, 3.3 mmol) in 30 ml of anhydrous N,N-dimethyl formamide at 0° C. After stirring at 0° C. for 15 min and additional 30 min at room temperature, the mixture was cooled again to 0° C. and methoxymethyl bromide (1.27 g, 10.2 mmol) was added. After stirring at 0° C. for 30 min, stirring was continued for another 120 min at room temperature. Methanol and $H_2O$ were added to destroy excess of sodium hydride. The mixture was extracted with ehtyl acetate (3×60 ml), the combined organic layers were washed with $H_2O$ (2×50 ml) and brine (2×50 ml) and evaporated to give a yellowish oil which was purified by column chromatography (silica gel, elution with $CH_2Cl_2$/MeOH/conc. $NH_4OH$ 245:10:1) to afford 500 mg (30%) pure compound 2 as a colorless foam.

$^1$H NMR ($CDCl_3$): δ 7.44 (m, 2 arom. H), 7.20 (m, 1 arom. H), 7.07 (m, 1 arom. H), 6.82 (d, J=8 Hz, 1 arom. H), 6.58 (J=8 Hz), 5.81 (s, H—C(5)), 5.79 and 5.50 (2 d, J=10.8, 10.8 Hz, $NCH_2O$) 5.12 and 5.50 (2 d, J=6.4, 6.4 Hz, $OCH_2O$), 3.41 and 3.33 (2 s, $CH_3O$). Analysis calculated for $C_{30}H_{34}N_2O_5$ (502.61): C 71.69, H 6.82, N 5.57; found: C 71.92, H 6.94, N 5.34.

Example 3

Synthesis of 17-(Cyclopropylmethyl)-6,7-dehydro-14-(2',6'-dichlorobenzyloxy)-4,5α-epoxy-3-(methoxymethoxy)-6,7-2',3'-benzo[b]furanomorphinan (compound 3).

Sodium hydride (36 mg, 1.5 mmol; obtained from 60 mg of 60% sodium hydride dispersion in oil by washings with n-hexane) was added to a solution of compound 1 (300 mg, 0.65 mmol) in 8 ml of anhydrous N,N-dimethylformamide at 0° C. After stirring at 0° C. for 15 min, stirring was continued for another 30 min at room temperature and the mixture was cooled again to 0° C. 2,6-Dichlorobenzyl bromide (240 g, 1 mmol) was added at once and stirring was continued for 15 min at 0° C. and then for 3 h at room temperature. Excess sodium hydride was destroyed with MeOH and $H_2O$ and the mixture was extracted with ethyl acetate (3×30 ml). The combined organic layers were washed with $H_2O$ (2×30 ml) and brine (2×30 ml), dried over $Na_2SO_4$ and evaporated. The residue (400 mg colorless oil) was crystallized from MeOH to yield 300 mg (75%) of compound 3. M. p. 180–1820 C.

$^1$H NMR ($CDCl_3$): δ 7.41 (d, J=8.3 Hz, 1 arom. H), 7.33 (d, J=8.3 Hz, 1 arom. H), 7.23 (m, 1 arom. H), 7.14 (m, 2 arom. H), 7.03 and 7.01 (2 d, J=7.3, 7.3 Hz, 2 arom. H), 6.84 (d, J=8.3 Hz, 1 arom. H), 6.59 (d, J=8.3 Hz, 1 arom. H), 5.56 (s, H-C(5)), 5.32 and 4.68 (2 d, J=8.7, 8.7 Hz, $OCH_2Ph$), 5.16 and 5.05 (2 d, J=6.6, 6.6 Hz, $OCH_2O$), 3.41 (s, $CH_3O$).

Example 4

Synthesis of 17-(Cyclopropylmethyl)-6,7-dehydro-14-(2',6'-dichlorobenzyloxy)-4,5α-epoxy-3-hydroxy-6,7-2',3'-benzo[b]furanomorphinan (compound 4).

A solution of compound 3 (150 mg, 0.24 mmol) in MeOH (4 ml) and 1N HCl (2 ml) was refluxed for 1 h. After cooling, the solution was alkalized with conc. $NH_4OH$, extracted wiht ethyl acetate (3×15 ml), the combined organic layers were washed with $H_2O$ (2×15 ml) and brine (10 ml), dried over $Na_2SO_4$ and evaporated to give an oily residue which was crystallized from MeOH to yield 70 mg (51%) of compound 4. M. p. 193–195° C. (dec.).

$^1$H NMR ($CDCl_3$): δ 7.42 (d, J=8.3 Hz, 1 arom. H), 7.33 (d, J=8 Hz, 1 arom. H), 7.24 (m, 1 arom. H), 7.14 (m, 2 arom. H), 7.03 and 7.01 (2 d, J=7.3 Hz, 1 arom. H), 6.64 (d, J=8.1 Hz, 1 arom. H), 6.56 (d, J=8.1 Hz, 1 arom. H), 5.58 (s, H—C(5)), 5.32 and 4.68 (2 d, J=8.6 Hz, $OCH_2Ph$). Analysis calculated for $C_{33}H_{29}Cl_2NO_4$ (574.51): C 68.79, H 5.09, N 2.44; found: C 68.97, H 5.05, N 2.44.

Example 5

Synthesis of 17-(Cyclopropylmethyl)-6,7-dehydro-4,5α-epoxy-3-(methoxymethoxy)-14-(3'-nitrobenzyloxy)-6,7-2',3'-benzo[b]furanomorphinan (compound 5).

Sodium hydride (36 mg, 1.5 mmol; obtained from 60 mg of 60% sodium hydride dispersion in oil by washings with n-hexane) was added to a solution of compound 1 (300 mg, 0.65 mmol) in 6 ml of anhydrous N,N-dimethylformamide at 0° C. The resulting mixture was stirred at 0° C. for 15 min and then at room temperature for another 30 min. After cooling to 0° C., 3-nitrobenzyl bromide (216 mg, 1 mmol) was added and stirring was continued first at 0° C. for 15 min and then at room temperature for 3 h. Excess sodium hydride was destroyed by addition of MeOH and $H_2O$. The resulting mixture was extracted with ethyl acetate (3×30 ml), the combined organic layers were washed with $H_2O$ (2×20 ml) and brine (2×20 ml), dried over $Na_2SO_4$ and evaporated to give 380 mg of a brown oil which was purified by column chromatography (silica gel, elution with $CH_2Cl_2$/MeOH/ conc. $NH_4OH$ 240:10:1) to afford 100 mg (26%) of compound 5 as colorless foam.

$^1$H NMR ($CDCl_3$): δ 8.25 (s, 1 arom. H), 7.99 (m, 1 arom. H), 7.55 (d, J=7.8 Hz, 1 arom. H), 7.47 (d, J=8.3 Hz, 1 arom. H), 7.28 (m, 4 arom. H), 7.15 (m, 1 arom. H), 6.87 (d, J=8.3 Hz, 1 arom. H), 6.62 (d, J=8.3 Hz, 1 arom. H), 5.66 (s, H—C(5)), 5.17 and 5.07 (2 d, J=6.6 Hz, $OCH_2O$), 4.92 and 4.44 (2 d, J=11.5 Hz, $OCH_2Ph$), 3.42 (s, $CH_3O$).

Example 6

Synthesis of 17-(Cyclopropylmethyl)-6,7-dehydro-4,5α-epoxy-3-hydroxy-14-(3'-nitrobenzyloxy)-6,7-2',3'-benzo[b]furanomorphinan Hydrochloride (compound 6).

A solution of compound 5 (80 mg, 0.13 mmol) in MeOH (4 ml) and 1N HCl (2 ml) was refluxed for 1 h. After cooling, the solution was alkalized with conc. $NH_4OH$, extracted with ethyl acetate (3×20 ml), the combined organic layers were washed with $H_2O$ (2×15 ml) and brine (15 ml), dried over $Na_2SO_4$ and evaporated. The oily residue was dissolved in acetone and transformed into the hydrochloride salt (compound 6) by addition of ethereal HCl. Yield 50 mg (66%). M. p.>230° C. (dec.).

$^1$H NMR (DMSO-$d_6$): δ 9.40 (s, OH), 9.15 (broad s, $^+$NH), 7.84 (s, 1 arom. H), 7.60 (d, J=8.8 Hz, 1 arom. H), 7.53 (d, J=7.6 Hz, 1 arom. H), 7.45 (d, J=8 Hz, 1 arom. H), 7.23 (d, J=7.6 Hz, 1 arom. H), 7.19 (d, J=7.6 Hz, 1 arom. H), 6.98 (m, 1 arom. H), 6.88 (d, J=7.6 Hz, 1 arom. H), 6.69 (d, J=8.3 Hz, 1 arom. H), 6.66 (d, J=8.3 Hz, 1 arom. H), 6.03 (s, H—C(5)), 4.98 and 4.87 (2 d, J=14, 14 Hz, $OCH_2Ph$). Analysis calculated for $C_{33}H_{30}N_2O_6$×HCl (587.08): C 67.52, H 5.32, N. 4.77; found: C 67.78, H 5.25, N 4.76.

Example 7

Synthesis of 17-(Cyclopropylmethyl)-6,7-dehydro-4,5α-epoxy-3-(methoxymethoxy)-14-(2-naphthylmethoxy)-6,7-2',3'-benzo[b]furanomorphinan (compound 7).

Sodium hydride (36 mg, 1.5 mmol; obtained from 60 mg of sodium hydride dispersion in oil by washings with n-hexane) was added to a solution of compound 1 (300 mg, 0.65 mmol) in 5 ml of anhydrous N,N-dimethylformamide at 0° C. The resulting mixture was stirred at 0° C. for 15 min and then at room temperature for another 30 min. After cooling to 0° C., 2-(bromomethyl)naphthalene (221 mg, 1 mmol) was added and stirring was continued at first at 0° C. for 15 min and then at room temperature for 2 h. Excess sodium hydride was destroyed by addition of MeOH and $H_2O$. The resulting mixture was extracted with ethyl acetate (3×30 ml), the combined organic layers were washed with $H_2O$ (2×20 ml) and brine (2×10 ml), dried over $Na_2SO_4$ and evaporated to give a crystalline residue which was recrystallized to yield 285 mg (73%) of compound 7. M. p. 198–201° C.

$^1$H NMR ($CDCl_3$): δ 7.72–7.08 (m, 11 arom. H), 6.86 (d, J=8.3 Hz, 1 arom. H), 6.62 (d, J=8.3 Hz, 1 arom. H), 5.68 (s, H—C(5)), 5.17 and 5.07 (2 d, J=6.6, 6.6 Hz, $OCH_2O$), 5.01 and 4.57 (2 d, J=11.2, 11.2 Hz, $OCH_2Ar$), 3.42 (s, $CH_3O$). Analysis calculated for $C_{39}H_{37}NO_5$×0.2EtOAc ($C_4H_8O_2$) (617.35): C77.43, H 6.30, N 2.27; found: C 77.40, H 6.27, N 2.27.

Example 8

Synthesis of 17-(Cyclopropylmethyl)-6,7-dehydro-4,5α-epoxy-3-hydroxy-14-(2'-naphthylmethoxy)-6,7-2',3'-benzo[b]furanomorphinan hydrochloride(compound 8).

A solution of compound 7 (180 mg, 0.3 mmol) in MeOH (5 ml) and 1N HCl (3 ml) was refluxed for 30 min, cooled and kept in the refrigerator overnight. The crystals formed were isolated and washed with small amounts of MeOH and ether to yield 150 mg (84%) of compound 8. M. p.>215° C.

$^1$H NMR (DMSO-$d_6$): δ 9.42 (s, OH), 9.00 (broad s, +NH), 7.68–6.85 (m, 11 arom. H), 6.71 (d, J=8 Hz, 1 arom. H), 6.67 (d, J=8 Hz, 1 arom. H), 6.04 (s, H-C(5)), 4.92 (s, $OCH_2Ar$). Analysis calculated for $C_{37}H_{33}NO_4$×HCl. 0.3 MeOH (601.75): C74.45, H 5.90, N 2.33; found: C 74.47, H 5.76, N 2.35.

Example 9

Synthesis of 17-(Cyclopropylmethyl)-6,7-dehydro-4,5α-epoxy-14-(2'-fluorobenzyloxy)-3-(methoxymethoxy)-6,7-2',3'-benzo[b]furanomorphinan (compound 9).

Sodium hydride (36 mg, 1.5 mmol; obtained from 60 mg of 60% sodium hydride dispersion in oil by washings with n-hexane) was added to a solution of compound 1 (300 mg, 0.65 mmol) in 5 ml of anhydrous N,N-dimethylformamide at 0° C. The resulting mixture was stirred at 0° C. for 10 min and the at room temperature for another 30 min. After cooling to 0° C., 2-flourobenzyl bromide (120 μl, 1 mmol) was added and stirring was continued at first at 0° C. for 15 min and then at room temperature for 2 h. Excess sodium hydride was destroyed by addition of MeOH and $H_2O$. The resulting mixture was extracted with ethyl acetate (3×30 ml), the combined organic layers were washed with $H_2O$ (2×20 ml) and brine (2×20 ml), dried over $Na_2SO_4$ and evaporated to give an oil which purified by column chromatography (silica gel, elution with ethyl acetate/n-hexane 1) 1:3 2) 1:1) to afford 215 mg (58%) of compound 9 as colorless foam.

$^1$H NMR (DMSO-$d_6$): δ 7.56 (d, J=8 Hz, 1 arom. H), 7.49 (d, J=8 Hz, 1 arom. H), 7.31 (m, 1 arom. H), 7.21 (m, 1 arom. H), 6.81 (d, J=8.4 Hz, 1 arom. H), 6.67 (d, J=8.4 Hz), 5.72 (s, H—C(5)), 5.06 and 5.01 (2 d, J=6.4, 6.4 Hz, $OCH_2O$), 4.89 and 4.57 (2 d, J=11.6, 11.6 Hz, $OCH_2Ph$), 3.33 (s, $CH_3O$). Analysis calculated for $C_{35}H_{34}NO_5$ (567.66): C 74.06, H 6.04, N 2.47; found: C 73.71, H 5.92, N 2.42.

Example 10

Synthesis of 17-(Cyclopropylmethyl)-6,7-dehydro-4,5α-epoxy-14-(2'-fluorobenzyloxy)-3-hydroxy-6,7-2',3'-benzo[b]furanomorphinan Hydrochloride (compound 10).

A solution of compound 9 (160 mg, 0.28 mmol) in MeOH (3 ml) and 1N HCl (3 ml) was refluxed for 20 min, then cooled and kept in the refrigerator overnight. The crystals formed were isolated and washed with small amounts of MeOH and ether to yield 110 mg (70%) of compound 10. M. p.>215° C.

$^1$H NMR ($CDCl_3$): δ 9.45 (s, OH), 9.04 (broad s, $^+$NH), 7.54 (d, J=8.4 Hz, 1 arom. H, 7.31–6.73 (m, 7 arom. H), 6.71 (d, J=8.2 Hz, 1 arom. H), 6.66 (d, J=8.2 Hz, 1 arom. H), 5.98

(s, H—C(5)), 4.81 and 4.84 (2 d, J=12 Hz, OCH$_2$Ph). Analysis calculated for C$_{33}$H$_{30}$FNO$_{4}$×HCl 1.4H$_2$O (585.29): C 67.72, H 5.82, N 2.39; found: C 67.63, H 5.56, N 2.51.

Example 11

Synthesis of 14(Cinnamyloxy)-17-(cyclopropylmethyl)-6,7-dehydro-4,5α-epoxy-3-(methoxymethoxy)-6,7-2',3'-benzo[b]furanomorphinan (compound 11).

Sodium hydride (36 mg, 1.5 mmol; obtained from 60 mg of 60% sodium hydride dispersion in oil by washings with n-hexane) was added to a solution of compound 1 (300 mg, 0.65 mmol) in 5 ml of anhydrous N,N-dimethylformamide at 0° C. The resulting mixture was stirred at 0° C. for 15 min and then at room temperature for another 30 min. After cooling to 0° C., cinnamyl bromide (197 mg, 1 mmol) was added and stirring was continued first at 0° C. for 10 min and then at room temperature for 2 h. Excess sodium hydride was destroyed by addition of MeOH and H$_2$O. The resulting mixture was extracted with ethyl acetate (3×30 ml), the combined organic layers were washed with H$_2$O (2×20 ml) and brine (1×20 ml), dried over Na$_2$SO$_4$ and evaporated to give a crystalline residue which was treated with boiling methanol to afford 200 mg (53%) of compound 11. M. p. 156–159° C.

$^1$H NMR (CDCl$_3$): δ 7.47 (d, J=8 Hz, 1 arom. H), 7.33 (d, J=8 Hz, 1 arom. H), 7.28–7.07 (m, 7 arom. H), 6.84 (d, J, 8.4 Hz, 1 arom. H), 6.59 (d, J=8.4 Hz, 1 arom. H), 6.38 (d, J=16 Hz, 1 olef. H), 6.13 (m, 1 olef. H), 5.68 (s, H—C(5)), 5.16 and 5.06 (2 d, J=6.4, 6.4 Hz, OCH$_2$O), 4.46 and 4.11 (2 m, CH$_2$O—C(14)), 3.42 (s, CH$_3$O). Analysis calculated for C$_{37}$H$_{37}$NO$_5$. 0.1 EtOAc (584.52): C 76.85, H 6.52, N 2.40; found: C 76.70, H 6.48, N 2.41.

Example 12

Synthesis of 14-(Cinnamyloxy)-17-(cyclopropylmethyl)-6,7-dehydro-4,5α-epoxy-3-hydroxy-6,7-2',3'-benzo[b]furanomorphinan Salicylate (compound 12).

A solution of compound 11 (160 mg, 0.28 mmol) in MeOH (3 ml) and 1N HCl (3 ml) was refluxed for 1 h. After cooling, the solution was alkalized with conc. NH$_4$OH, extracted with ethyl acetate (3×15 ml), the combined organic layers were washed with H$_2$O (2×15 ml) and brine (10 ml), dried over Na$_2$SO$_4$ and evaporated to give a colorless foam (100 mg). To a solution of this foam in a small amount of methanol 30 mg of salicyclic acid were added, the crystals formed collected and washed with cold methanol to yield 100 mg (53%) of compound 12. M. p.>170° C.

$^1$H NMR (CDCl$_3$): δ 7.94 (d, J=8 Hz, 1 arom. H), 7.35 (d, J=8 Hz, 1 arom. H), 7.30–6.73 (m, 12 arom. H), 6.56 (d, J=8 Hz, 1 arom. H), 5.96 (s, 2 olef. H), 5.55 (s, H—C(5)), 4.33–4.02 (m, CH$_2$O-C(14)). Analysis calculated for C$_{35}$H$_{33}$NO$_4$. Salicyclic acid (C$_7$H$_6$O$_3$). 1 MeOH (701.82): C 73.57, H 6.18, N 2.00; found: C 73.56, H 5.96, N 2.06.

Example 13

Synthesis of 17-(Cyclopropylmethyl)-6,7-dehydro-4,5α-epoxy-14-methoxy-3-(methoxymethoxy)-6,7-2',3'-benzo[b]furanomorphinan (compound 13).

Sodium hydride (36 mg, 1.5 mmol; obtained from 60 mg of 60% sodium hydride dispersion in oil by washings with n-hexane) was added to a solution of compound 1 (300 mg, 0.65 mmol) in 5 ml of anhydrous N,N-dimethylformamide at 0° C. The resulting mixture was stirred at 0° C. for 15 min and the at room temperature for another 30 min. After cooling to 0° C., dimethyl sulfate (100 μl, 1 mmol) was added and stirring was continued at first at 0° C. for 15 min and then at room temperature for 2 h. Excess sodium hydride was destroyed by addition of MeOH and H$_2$O. The resulting mixture was extracted with ethyl acetate (3×30 ml), the combined organic layers were washed with H$_2$O (2×20 ml) and brine (2×20 ml), dried over Na$_2$SO$_4$ and evaporated to give a colorless foam (280 mg) of compound 13 which was pure by TLC and NMR.

$^1$H NMR (DMSO-d$_6$): δ 7.56 (d, J=8 Hz, 1 arom. H), 7.52 (d, J=8 Hz, 1 arom. H), 7.32 (dd, J=8, 8 Hz, 1 arom. H), 7.23 (dd, J=8, 8 Hz, 1 arom. H), 6.79 (d, J=8.2 Hz, 1 arom. H), 6.64 (d, J=8.2 Hz, 1 arom. H), 5.64 (s, H—C(5)), 5.05 and 5.00 (2 d, J=6.4, 6.4 Hz, OCH$_2$O), 3.32 (CH$_3$0). Analysis calculated for C$_{29}$H$_{31}$NO$_5$. 0.2MeOH (479.98): C 73.07, H 6.68, N 2.92; found: C 72.94, H 6.60, N 2.92.

Example 14

Synthesis of 17-(Cyclopropylmethyl)-6,7-dehydro-4,5α-epoxy-3-hydroxy-14-methoxy-6,7-2',3'-benzo[b]furanomorphinan Hydrochloride (compound 14).

A solution of compound 13 (160 mg, 0.28 mmol) in MeOH (3 ml) and 1N HCl (2 ml) was refluxed for 20 min, then cooled and kept in the refrigerator overnight. The crystals formed were isolated and washed with small amounts of MeOH and ether to yield 70 mg (36%) of compound 14. M. p.>240° C.

$^1$H NMR (DMSO-d$_6$): δ 9.47 (s, OH), 9.17 (broad s, +NH), 7.61 (d, J=8 Hz, 1 arom. H), 7.53 (d, J=8 Hz, 1 arom. H), 7.36 (dd, J=8, 8 Hz, 1 arom. H), 7.27 (dd, J=8, 8 Hz, 1 arom. H), 6.72 (d, J=8.4 Hz, 1 arom. H), 6.65 (d, J=8.4 Hz, 1 arom. H), 5.90 (s, H—C(5)), 3.35 (s, CH$_3$O). Analysis calculated for C$_{27}$H$_{27}$NO$_4$×HCl. 1.5 H$_2$O (493.00): C 65.78, H 6.34, N 2.84; found: C 65.89, H 6.20, N 2.85.

Example 15

Synthesis of 17-(Cyclopropylmethyl)-14-(2'-chlorobenzyloxy)-6,7-dehydro-4,5α-epoxy-3-(methoxymethoxy)-6,7-2',3'-(N-methoxymethylindolo)morphinan (compound 15).

Sodium hydride (36 mg, 1.5 mmol; obtained from 60 mg of 60% sodium hydride dispersion in oil by washings with n-hexane) was added to a solution of compound 2 (327 mg, 0.65 mmol) in 5 ml of anhydrous N,N-dimethylformamide at 0° C. The resulting mixture was stirred at 0° C. for 15 min and then at room temperature for another 30 min. After cooling to 0° C., 2-chlorobenzyl bromide (205 mg, 1 mmol) was added and stirring was continued first at 0° C. for 15 min and then at room temperature for 3 h. Excess sodium hydride was destroyed by addition of MeOH and H$_2$O. The resulting mixture was extracted with ethyl acetate (3×30 ml), the combined organic layers were washed with H$_2$O (2×40 ml) and brine (2×30 ml), dried over Na$_2$SO$_4$ and evaporated to give 370 mg of compound 15 as colorless foam which was pure by TLC and NMR.

$^1$H NMR (CDCl$_3$): δ 7.56 (m, 1 arom. H), 7.44 (m, 1 arom. H), 7.37–7.17 (m, 3 arom. H), 7.01 (m, 1 arom. H), 6.91 (m, 1 arom. H), 6.83 (d, J=8.2 Hz, 1 arom. H), 6.59 (d, J=8.2 Hz, 1 arom. H), 5.90 (s, H—C(5)), 5.82 and 5.55 (2 d, J=11.2, 11.2 Hz, NCH$_2$O), 5.13 and 5.03 (2 d, J=6.4, 6.4 Hz, OCH$_2$O), 4.98 and 4.56 (2 d, J=13, 13 Hz, OCH$_2$Ph), 3.40 and 3.26 (2 s, 2 CH3O).

Example 16

Synthesis of 17-(Cyclopropylmethyl)-14-(2'-chlorobenzyloxy)-6,7-dehydro-4,5α-epoxy-3-hydroxy-6,7-2',3'-indolomorphinan Hydrochloride (compound 16).

A solution of compound 15 (300 mg, 0.48 mmol) in MeOH (5 ml) and 1N HCl (3 ml) was refluxed for 1 h. After cooling, the solution was alkalized with conc. $NH_4OH$, extracted with ethyl acetate (3×20 ml), the combined organic layers were washed with $H_2O$ (2×20 ml) and brine (20 ml), dried over $Na_2SO_4$ and evaporated to give a colorless oil. To a solution of this foam in a small amount of methanol ethereal HCl was added, the crystals formed collected and washed with cold methanol to yield 120 mg (43%) of compound 16. M. p.>250° C. (dec.).

$^1$H NMR (DMSO-$d_6$): δ 11.38 (s, NH), 9.38 (s, OH), 8.76 (broad s, ±NH), 7.34–6.85 (m, 8 arom. H), 6.72 (d, J=8 Hz, 1 arom. H), 6.64 (d, J=8 Hz, 1 arom. H), 5.93 (s, H—C(5)), 4.80 and 4.67 (2 d, J=13, 13 Hz, $OCH_2Ph$). Analysis calculated for $C_{33}H_{31}N_2O_3$×HCl. (575.54): C 68.87, H 5.60, N 4.87; found: C 68.81, H 5.59, H 4.77.

Example 17

Synthesis of 17-(Cyclopropylmethyl)-6,7-dehydro-3,14dimethoxy-4,5α-epoxy-6,7-2',3'-benzo[b]furanomorphinan (compound 17).

Sodium hydride (144 mg, 6 mmol; obtained from 240 mg of 60% sodium hydride dispersion in oil by washings with n-hexane) was added to a solution of naltriben methanesulfonate (500 mg, 0.97 mmol) in 10 ml of anhydrous N,N-dimethylformamide at 0° C. The resulting mixture was stirred at 0° C. for 15 min and then at room temperature for another 30 min. After cooling to 0° C., dimethyl sulfate (380 μl, 4 mmol) was added and stirring was continued first at 0° C. for 30 min and then at room temperature for 3 h. Excess sodium hydride was destroyed by addition of MeOH and $H_2O$. The resulting mixture was extracted with ethyl acetate (3×40 ml), the combined organic layers were washed with $H_2O$ (2×30 ml) and brine (2×30 ml), dried over $Na_2SO_4$ and evaporated to give a crystalline residue which was recrystallized from MeOH to afford 320 mg (74%) of compound 17. M. p. 221–224° C. (dec.).

$^1$H NMR ($CDCl_3$): δ 7.47–7.14 (m, 4 arom. H), 6.64 (d, J=8.4 Hz, 1 arom. H), 6.59 (d, J=8.4 Hz, 1 arom. H), 5.62 (s, H—C(5)), 3.78 (s, $CH_3O$—C(3)), 3.31 (s, $CH_3O$—C(14)). Analysis calculated for $C_{28}H_{29}NO_4$. 0.3 MeOH (453.16): C 75.01, H 6.72, N 3.09; found: C 74.97, H 6.68, N 3.05.

Example 18

Synthesis of 17-(Cyclopropylmethyl)-6,7-dehydro-4,5α-epoxy-3-hydroxy-14-(3'-chlorobenzyloxy)-6,7-2',3'-benzo[b]furanomorphinan Hydrochloride (compound 19).

To a stirred solution of naltriben methanesulfonate (256 mg, 0.5 mmol) in anhydrous N,N-dimethyl formamide (10 ml) was added sodium hydride (60% dispersion in oil, 60 mg, 1.5 mmol) at 0° C. The solution was stirred for 1 h at 20° C. and then cooled to 0° C. prior to addition of bromomethyl methyl ether (125 mg, 1.0 mmol). The mixture was warmed up to room temperature during 1 h and cooled again to 0° C. before sodium hydride (60% dispersion in oil, 100 mg, 2.5 mmol) was added. After 1 h, 3-chlorobenzyl bromide (308 mg, 1.5 mmol) was added to the solution and the resulting mixture was stirred for 4 h at 200 C., and then 5 ml of methanol and 5 ml ethyl acetate were slowly added at 0° C., followed by addition of saturated aqueous $NH_4Cl$ solution (20 ml). The mixture was extracted with ethyl acetate (3×50 ml), the combined organic layers were washed with brine, dried over $MgSO_4$, and evaporated to give crude 17-(cyclopropylmethyl)-6,7-dehydro-4,5α-epoxy-3-(methoxymethoxy)-14-(3'-chlorobenzyloxy)-6,7-2',3'-benzo [b]furanomorphinan (compound 18). This crude product was dissolved in 5 ml of ethanol and 1.5 ml of 1N hydrochloric acid and refluxed for 1 h. The reaction mixture was alkalized with 1N aqueous $NH_4OH$ solution, extracted with ethyl acetate (3×50 ml), the combined organic layers were washed with brine, dried over $MgSO_4$, and concentrated to give a crude product which was purified by silica gel column chromatography (hexane: $CHCl_3$ (75:25→50:50→25:75→100:0)→$CHCl_3$:AcOEt (80:20→50:50→0:100) to afford the title compound as the free base (colorless oil; 232 mg, 86%). $^1$H NMR ($CDCl_3$): δ 7.50–7.05 (m, 8 arom. H), 6.69 (d, J=8.4 Hz, 1 arom. H), 6.58 (d, J=8.4 Hz, 1 arom. H), 5.68 (s, H—C(5)), 4.81 and 4.35 (2 d, J=11.6, 11.6 Hz, $OCH_2$(3'-ClPh)). A solution of this free base in anhydrous diethyl ether (5 ml) was treated with HCl/ether solution (1M, 2 ml) at 0° C. Isolation of the precipitate provided the title compound 19 as a solid. M. p.>230° C. (dec.). $^1$H NMR (DMSO-$d_6$): δ 9.40 (s, OH), 8.59 (broad s, $^+$NH), 7.53–6.90 (m, 8 arom. H), 6.65 (s, 2 arom. H) 6.03 (s, H—C(5)), 4.74 and 4.62 (2 d, J=13.6, 13.6 Hz, $OCH_2$(3'-ClPH)). Analysis calculated for $C_{33}H_{30}ClNO_4$. HCl. 1.5 $H_2O$: C 65.67, H 5.68, N 2.32; found: C 65.31, H 5.37, N 2.33.

Example 19

Synthesis of 17-(Cyclopropylmethyl)-6,7-dehydro-4,5α-epoxy-3-hydroxy-14-(2'-chlorobenzyloxy)-6,7-2',3'-benzo[b]furanomorphinan Hydrochloride (compound 21).

To a stirred solution of naltriben methanesulfonate (256 mg, 0.5 mmol) in anhydrous N,N-dimethyl formamide (10 ml) was added sodium hydride (60% dispersion in oil, 100 mg, 2.5 mmol) at 0° C. The solution was stirred for 1 h at 20° C. and then cooled to 0° C. prior to addition of bromomethyl methyl ether (125 mg, 1.0 mmol). The mixture was warmed up to room temperature during 1 h and cooled again to 0° C. before sodium hydride (60% dispersion in oil, 100 mg, 2.5 mmol) was added. After 1 h, 2-chlorobenzyl bromide (205 mg, 1.0 mmol) was added to the solution and the resulting mixture was stirred for 12 h at 20° C., and then 5 ml of methanol and 5 ml ethyl acetate were slowly added at 0° C., followed by addition of saturated aqueous $NH_4Cl$ solution (20 ml). The mixture was extracted with ethyl acetate (3×50 ml), the combined organic layers were washed with brine, dried over $MgSO_4$, and concentrated to give crude 17-(cyclopropylmethyl)-'6,7-dehydro-4,5α-epoxy-3-(methoxymethoxy)-14-(2'-chlorobenzyloxy)-6,7-2',3'-benzo[b]furanomorphinan (compound 20). This crude product was dissolved in 5 ml of ethanol and 2 ml of 1N hydrochloric acid and refluxed for 2 h. The reaction mixture was alkalized with 1N aqueous $NH_4OH$ solution, extracted with ethyl acetate (3×50 ml), the combined organic layers were washed with brine, dried over $MgSO_4$, and evaporated to give a crude product which was purified by silica gel column chromatography (hexane: $CHCl_3$ (75:25→50:50→25:75→100:0) to afford the title compound as the free base (colorless oil: 236 mg, 87%). $^1$H NMR ($CDCl_3$): δ 7.45–6.90 (m, 8 arom. H), 6.72 (d, J=8.4 Hz, 1 arom. H), 6.68 (d, J=8.4 Hz, 1 arom. H), 5.72 (s, H-C(5)), 4.96 and 4.55 (2 d, J=11.6, 11.6 Hz, $OCH_2$(2'-ClPh)). A solution of this free base in (5 ml) of anhydrous diethyl ether was treated with HCl/ether solution (1M, 2 ml) at 0° C. Isolation of the precipitate provided the title compound as a solid. M. p.>220° C.

$^1$H NMR (DMSO-$d_6$): δ 9.40 (s, OH), 8.59 (broad s, $^+$NH), 7.56–6.90 (m, 8 arom. H), 6.66 (s, 2 arom. H) 6.03 (s, H—C(5)), 4.74 (s, $OCH_2$(2'-ClPh)). Analysis calculated for $C_{33}H_{30}ClNO_4$×HCl. 1.5 $H_2O$: C 65.67, H 5.68, N 2.32; found: C 65.72, H 5.48, N 2.25.

Example 20

Synthesis of 14-Allyloxy-17-(cyclopropylmethyl)-6,7-dehydro-4,5α-epoxy-3-hydroxy-1'-allyl-6,7-2',3'-indolomorphinan Hydrochloride (compound 22).

Dimethyl isobutylsilyl chloride (114 mg, 0.75 mmol) was added at 0° C. to a stirred solution of naltrindole methanesulfonate (255 mg, 0.5 mmol) and diisopropyl ethylamine (260 mg, 2.0 mmol) in anhydrous N,N-dimethyl formamide (10 ml). The resulting solution was stirred at 20° C. for 1 h and then cooled to 0° C. prior to the addition of sodium hydride (60% dispersion in oil, 120 mg, 3.0 mmol). After 1 h, dimethyl isobutylsilyl chloride (114 mg, 0.75 mmol) was added to the mixture. The resulting mixture was stirred for 1 h at 20° C. and then cooled to 0° C. before adding sodium hydride (60% dispersion in oil, 120 mg, 3.00 mmol). After 1 h allyl bromide (1.51 mg, 1.25 mmol) was added. The reaction mixture was stirred for 2 h at 20° C. and then quenched with saturated aqueous $NH_4Cl$ solution and extracted with ethyl acetate (3×30 ml). The combined organic layers were washed with brine, dried over $MgSO_4$, and evaporated to give a yellow oil which was dissolved in methanol (6 ml) and 1 N hydrochloric acid (2 ml) and refluxed for 6 h. The reaction mixture was alkalized with 1N $NH_4OH$ solution, extracted with ethyl acetate (3×30 ml), the combined organic layers were washed with brine, dried over $MgSO_4$, and evaporated. This crude product was purified by silica gel column chromatography (hexane: $CHCl_3$ (75:25→50:50)→$CHCl_3$:AcOEt→(75:25→50:50→AcOEt) to give the title compound as the free base (colorless oil; 106 mg).

$^1$H NMR ($CDCl_3$): 67.40 (d, J=8.4 Hz, 1 arom. H), 7.24 (m, 1 arom. H), 7.15 (m, 1 arom. H), 7.03 (m, 1 arom. H), 6.57 (d, J=8.4 Hz, 1 arom. H), 6.50 (d,J=8.4 Hz, 1 arom. H), 6.08 (m, 1 olef. H), 5.76 (m, 1 olef. H), 5.72 (s, H-C(5)), 5.15–4.75 (m, 6H, $CH_2N$, 2 $CH_2$=C), 4.24 and 3.92 (2 dd, J=12.4, 4.8 Hz, $CH_2O$).

The free base was dissolved in diethyl ether (5 ml) and treated with HCl/ether solution (1M, 2 ml) at 0° C. Isolation of the precipitate provided the title compound 22 as a solid.

Example 21

Synthesis of 17-(Cyclopropylmethyl)-6,7-dehydro-4,5α-epoxy-3-hydroxy-14-allyloxy-6,7,2',3'-indolomorphinan Hydrochloride (compound 23)

To a stirred solution of naltrindole hydrochloride (220 mg, 0.5 mmol) in anhydrous N,N-dimethyl formamide (10 ml) was added sodium hydride (60% dispersion in oil, 160 mg, 4.0 mmol) at 0C. The solution was stirred for 1 h at 20° C., and then cooled to 0° C. prior to addition of bromomethyl methyl ether (250 mg, 2.0 mmol). The mixture was warmed up to r.t. during one hour and cooled again to 0° C. before sodium hydride (60%, 100 mg, 2.5 mmol) was added. After 1 h allyl bromide (242 mg, 2.0 mmol) was added to the solution and the resulting mixture was stirred for 4 h at 20° C., and then 5 ml methanol and 5 ml ethyl acetate were slowly added at 0° C., followed by addition of saturated aqueous $NH_4Cl$ solution (20 ml). The mixture was extracted with ethyl acetate (3×50 ml), the combined organic layers were washed with brine, dried over $MgSO_4$, and evaporated to give crude product, which was dissolved in 5 ml ethanol/1 ml 6N hydrochloric acid and refluxed for 2 hrs. The reaction mixture was alkalized with 1 N aqueous $NH_4OH$ solution, extracted with ethyl acetate (3.50 ml), the combined organic layers were washed with brine, dried over $MgSO_4$, and concentrated to give a crude product, which was purified by silica gel column chromatography (Hexane: $CHCl_3$ (75:25→50:50→25:75→0:100)→$CHCl_3$:AcOEt (75:25→50:50→40:100)) to afford compound 23 (53 mg, 23%) as the free base (colorless oil). 1 H NMR ($CDCl_3$): δ 7.50–7.00 (m, 4 arom. H), 6.65–6.45 (m, 2 arom. H), 5.80 (m, 1H, CH=C), 5.75 (s, H—C(5)), 5.18–4.85 (m, C=$CH_2$), 4.25 & 3.95 (m, $OCH_2$).

A solution of this free base (53 mg) in anhydrous ethyl ether (5 ml) was treated with HCl/ether solution (1 M, 1 ml) at 0° C. Isolation of the precipitate provided the title compound 23 as a solid (hydrochloride salt). M.p. 270–285° C. (dec.). IR (HCl salt, KBr) 3087 (m), 2846 (m), 1623 (s), 1505 (s), 1462 (s), 1330 (s), 1166 (s), 922 (s) $cm^{-1}$.

Example 22

Synthesis of 17-Cyclopropylmethyl-6,7-dehydro-4,5α-epoxy-3-hydroxy-14-benzyloxy-6,7,2',3'-benzo[b]foranomorphinan Hydrochloride (compound 24):

To a stirred solution of naltriben methanesulfonate (256 mg, 0.5 mmol) and N,N-diisopropylethylamine (260 mg, 2.0 mmol) in anhydrous N,N-dimethyl formamide (10 ml) was added triisopropylsilyl chloride (145 mg, 0.75 mmol) at 0° C. The solution was stirred for 1 h at 20° C., and then cooled to 0° C. prior to addition of sodium hydride (60%, 120 mg, 3.0 mmol) was added. After 1 h, benzyl bromide (171 mg, 1.0 mmol) was dropwise added to the solution. The resulting mixture was stirred for 2 h at 20° C., and then 5 ml methanol and 5 ml ethyl acetate were slowly added at 0° C. After 30 min the mixture was extracted with ethyl acetate (3×50 ml). The combined organic layers were washed with brine, dried over $MgSO_4$, and concentrated to a yellow oil, which was purified by silica gel column chromatography (Hexane: $CHCl_3$ (75:25→60:40)→Hexane: AcOEt (75:25→50:50)) to afford compound 24 (206 mg, 82%) as the free base (colorless oil). $^1$H NMR ($CDCl_3$): δ 7.60–7.05 (m, 9 arom. H), 6.80–6.60 (m, 2 arom. H), 5.72 (s, H—C(5)), 4.95 and 4.52 (2 d, J=11.6, 11.6 Hz, $OCH_2Ph$).

A solution of this free base in anhydrous ethyl ether (5 ml) was treated with HCl/ether solution (1M, 1 ml) at 0° C. Isolation of the precipitate provided the title compound 24 as a solid (hydrochloride salt). M.p. 255–270° C. (dec.). IR (HCl salt, KBr) 3642 (m), 3174 (s), 2936 (s), 1616 (s), 1500 (s), 1457 (s), 1309 (s), 1068 (s), 932 (s) $cm^{-1}$. Analysis calculated for $C_{33}H_{31}NO_4$. HCl. 0.80 $H_2O$: C 71.23, H 6.09, N, 2.52. Found: C 71.32, H 5.78, N 2.35.

Example 23

Synthesis of 17-(Cyclopropylmethyl)-6,7-dehydro-4,5α-epoxy-3-hydroxy-14-allyloxy-6,7,2',3'-benzo[b]foranomorphinan Hydrochloride (compound 25)

To a stirred solution of naltriben methanesulfonate (256 mg, 0.5 mmol) and N,N-diisopropylethylamine (260 mg, 2.0 mmol) in anhydrous N,N-dimethyl formamide (10 ml) was added triisopropylsilyl chloride (145 mg, 0.75 mmol) at 0° C. The solution was stirred for 1 h at 20° C., and then cooled to 0° C. prior to addition of sodium hydride (60%, 120 mg, 3.0 mmol) was added. After 1 h, allyl bromide (363 mg, 3.0 mmol) was dropwise added to the solution. The resulting mixture was stirred for 2 h at 20° C., and then 5 ml methanol and 5 ml ethyl acetate were slowly added at 0° C. After 30 min the mixture was extracted with ethyl acetate (3×50 ml). The combined organic layers were washed with brine, dried over $MgSO_4$, and concentrated to a yellow oil, which was dissolved in $MgSO_4$, and concentrated to a yellow oil, which was dissolved in 10 ml ethanol/2.0 ml 1N hydrochloric acid and refluxed for 5 hrs. The reaction mixture was alkalized with IN aqueous $N_4OH$ solution, extracted with ethyl acetate (3×50 ml). The combined organic layers were washed with brine, dried over MgSO$_4$, and concentrated to give a crude product, which was purified by silica gel column chromatography (Hexane: CHCl$_3$ (75:25→50:50)→CHCl$_3$:AcOEt (75:25→50:50→AcOEt)) to afford compound 25 (106 mg, 46%) as the free base (colorless oil). $^1$H NMR (CDCl$_3$): δ 7.50–7.08 (m, 4 arom. H), 6.70–6.45 (m, 2 arom. H), 5.75 (m, 1H, CH═C) 5.65 (s, H—C(5)), 5.18–4.82 (m, 2H), 4.81 (br s, OH), 4.25 and 3.90 (m, OCH$_2$).

A solution of this free base in anhydrous ethyl ether (5 ml) was treated with HCl/ether solution (1M, 1 ml) at 0° C. Isolation of the precipitate provided the title compound 25 as a solid (hydrochloride salt). M.p. 280–290° C. (dec.). IR (HCl salt, KBr) 3642 (m), 2948 (s), 1641 (s), 1500 (s), 1375 (s), 1315 (s), 996 (s) 920 (s) cm$^{-1}$. Analysis calculated for C$_{29}$H$_{29}$NO$_4$. HCl. 1.1H$_2$O: C 68.05, H 6.34, N, 2.74. Found: C 67.94, H 5.95, N 2.53.

Example 24

Synthesis of 1 7-(Cyclopropylmethyl)-6,7-dehydro-4,5α-epoxy-3-hydroxy-14-crotyloxy-6,7,2',3'-benzo[b]foranomorphinan Hydrochloride (compound 26)

To a stirred solution of naltriben methanesulfonate (256 mg, 0.5 mmol) and N,N-diisopropylethylamine (260 mg, 2.0 mmol) in anhydrous N,N-dimethyl formamide (10 ml) was added triisopropylsilyl chloride (145 mg, 0.75 mmol) at 0° C. The solution was stirred for 1 h at 20° C., and then cooled to 0° C. prior to addition of sodium hydride (60%, 120 mg, 3.0 mmol) was added. After 1 h, crotyl bromide (405 mg, 3.0 mmol) was dropwise added to the solution. The resulting mixture was stirred for 2 h at 20° C., and then 5 ml methanol and 5 ml ethyl acetate were slowly added at 0° C. After 30 min the mixture was extracted with ethyl acetate (3×50 ml). The combined organic layers were washed with brine, dried over MgSO$_4$, and concentrated to a yellow oil, which was dissolved in 10 ml ethanol/2 ml 1 N hydrochloric acid and refluxed for 5 hrs. The reaction mixture was alkalized with 1N aqueous NH$_4$OH solution, extracted with ethyl acetate (3—50 mld). The combined organic layers were washed with brine, dried over MgSO$_4$, and concentrated to give a crude product, which was purified by silica gel column chromatography (Hexane:CHCl$_3$ (75:25→50:50) →4CHCl$_3$:AcOEt (75:25→450:50→AcOEt)) to afford compound 26 (45 mg, 19%) as the free base (colorless oil). $^1$H NMR (CDCl$_3$): δ 7.48–7.08 (m, 4 arom. H), 6.66–6.48 (m, 2 arom. H), 5.62 (s, H—C(S)), 5.40 (m, 2H, CH═CH), 4.20 and 3.82 (m, OCH$_2$), 1.48 & 1.52 (m, 3H, Me).

A solution of the free base in anhydrous ethyl ether (5 ml) was treated with HCl/ether solution (1 M, 1 ml) at 0° C. Isolation of the precipitate provided the title compound 26 as a solid in form of its hydrochloride salt. Mp. 245–260° C. (dec.). IR (Hcl salt, Kbr): 3642 (m), 3024 (s), 1640 (s), 1503 (s), 1325 (s), 927 (s) cm$^{-1}$.

We claim:

1. A compound according to the formula (V)

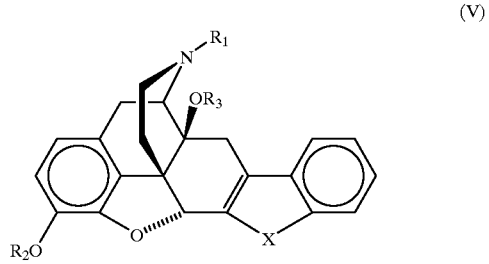

(V)

wherein

R$_1$ is allyl or cyclopropylmethyl;

R$_2$ is benzyl, methoxymethyl, ethoxymethyl, trityl or silyl; and

R$_3$ is C$_1$–C$_6$ alkyl, C$_1$–C$_6$ alkenyl; C$_7$–C$_{16}$ arylalkyl wherein the aryl is C$_6$–C$_{10}$ aryl and the alkyl is C$_1$–C$_6$ alkyl; C$_7$–C$_{16}$ arylalkenyl wherein the aryl C$_6$–C$_{10}$ aryl and the alkenyl is C$_1$–C$_6$ alkenyl; C$_1$–C$_6$ alkanoyl, C$_7$–C$_{16}$ arylalkanoyl wherein the aryl is C$_6$–C$_{10}$ aryl and the alkyl is C$_1$–C$_6$ alkyl;

X is NH, O, N-benzyl, N-methoxymethyl, N-ethoxymethyl, N-trityl, N-silyl, dimethyl isobutyl silyl, trimethylsilyl, triethylsilyl, t-butyldimethylsilyl or tri-i-propylsilyl; and with the proviso that when R$_1$ is cyclopropylmethyl, R$_2$ is methoxymethyl and R$_3$ is methyl, X is not O.

2. A compound according to formula (IV)

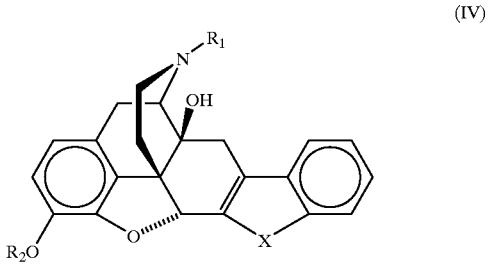

(IV)

wherein

R$_1$ is allyl, or cyclopropylmethyl or methyl;

R$_2$ is benzyl, methoxymethyl, ethoxymethyl, trityl, silyl, dimethyl isobutyl silyl, trimethylsilyl, triethylsilyl, t-butyldimethylsilyl or tri-i-propylsilyl; and X is NH, O, N-benzyl, N-methoxymethyl, N-ethoxymethyl, N-trityl, N-silyl, dimethyl isobutyl silyl, trimethylsilyl, triethylsilyl, t-butyldimethylsilyl or tri-i-propylsilyl;

and with the proviso that when R$_1$ is cyclopropylmethyl and R$_2$ is methoxymethyl, X is not O or N-methoxymethyl.

3. A compound according to the formula (VI)

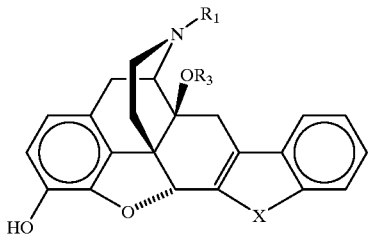

(VI)

wherein
R₁ is allyl or cyclopropylmethyl;
R₃ is $C_1$–$C_6$ alkyl, $C_1$–$C_6$ alkenyl; $C_7$–$C_{16}$ arylalkyl wherein the aryl is $C_6$–$C_{10}$ aryl and the alkyl is $C_1$–$C_6$ alkyl; $C_7$–$C_{16}$ arylalkenyl wherein the aryl is $C_6$–$C_{10}$ aryl and the alkenyl is $C_1$–$C_6$ alkenyl; $C_7$–$C_{16}$ arylalkanoyl wherein the aryl is $C_6$–$C_{10}$ aryl and the alkyl is $C_1$–$C_6$ alkyl; and
X is NH, O or N-benzyl.

4. A compound selected from the group consisting of:
17-(cyclopropylmethyl)-6,7-dehydro-4,5α-epoxy-14-hydroxy-3-(methoxymethoxy)-6,7-2',3'-benzo[b]furanomorphinan;
17-(cyclopropylmethyl)-6,7-dehydro-4,5α-epoxy-14-hydroxy-3-(methoxymethoxy)-6,7-2',3'-(N-methoxymethylindolo)morphinan;
17-(cyclopropylmethyl)-6,7-dehydro-14-(2',6'-dichlorobenzyloxy)-4,5α-epoxy-3-(methoxymethoxy)-6,7-2',3'-benzo[b]furanomorphinan;
17-(cyclopropylmethyl)-6,7-dehydro-14-(2',6'-dichlorbenzyloxy)-4,5α-epoxy-3-hydroxy-6,7-2',3'-benzo[b]furanomorphinan;
17-(cyclopropylmethyl)-6,7-dehydro-4,5α-epoxy-3-(methoxymethoxy)-14-(3'-nitrobenzyloxy)-6,7-2',3'-benzo[b]furanomorphinan;
17-(cyclopropylmethyl)-6,7-dehydro-4,5α-epoxy-3-hydroxy-1 4-(3'-nitrobenzyloxy)-6,7-2',3'-benzo[b]furanomorphinan hydrochloride;
17-(cyclopropylmethyl)-6,7-dehydro-4,5α-epoxy-3-(methoxymethoxy)-14-(2-naphthylmethoxy)-6,7-2',3'-benzo[b] furanomorphinan;
17-(cyclopropylmethyl)-6,7-dehydro-4,5α-epoxy-3-hydroxy-14-(2'-naphthylmethoxy)-6,7-2',3'-benzo[b]furanomorphinan hydrochloride;
17-(cyclopropylmethyl)-6,7-dehydro-4,5α-epoxy-14-(2'-fluorobenzyloxy)-3-(methoxymethoxy)-6,7-2',3'-benzo[b]furanomorphinan;
17-(cyclopropylmethyl)-6,7-dehydro-4,5α-epoxy-14-(2'-fluorobenzyloxy)-3-hydroxy-6,7-2'-3'-benzo[b]furanomorphinan hydrochloride;
14-(cinnamyloxy)-17-(cyclopropylmethyl)-6,7-dehydro-4,5α-epoxy3-(methoxymethoxy)-6,7-2',3'-benzo[b] furanomorphinan;
14-(cinnamyloxy)-17-(cyclopropylmethyl)-6,7-dehydro-4,5α-epoxy-3-hydroxy-6,7-2',3'-benzo[b]furanomorphinan salicylate;
17-(cyclopropylmethyl)-6,7-dehydro-4,5α-epoxy-14-methoxy-3-(methoxymethoxy)-6,7-2',3'-benzo[b]furanomorphinan;
17-(cyclopropylmethyl)-6,7-dehydro-4,5α-epoxy-3-hydroxy-14-methoxy-6,7-2',3'-benzo[b]furanomorphinan hydrochloride;
17-(cyclopropylmethyl)-14-(2'-chlorobenzyloxy)-6,7-dehydro-4,5α-epoxy-3-(methoxymethoxy)-6,7-2',3'-(N-methoxymethylindolo)morphinan;
17-(cyclopropylmethyl)-14-(2'-chlorobenzyloxy)-6,7-dehydro-4,5α-epoxy-3-hydroxy-6,7-2',3'-indolomorphinan hydrochloride;
17-(cyclopropylmethyl)-6,7-dehydro-3,14-dimethoxy-4,5α-epoxy-6,7-2',3'-benzo[b]furanomorphinan;
17-(cyclopropylmethyl)-6,7-dehydro-4,5°-epoxy-3-hydroxy-14-(3'-chlorobenzyloxy)-6,7-2',3'-benzo[b] furanomorphinan hydrochloride;
17-(cyclopropylmethyl)-6,7-dehydro-4,5α-epoxy-3-hydroxy-14-(2'-chlorobenzyloxy)-6,7-2',3'-benzo[b]furanomorphinan hydrochloride;
14-allyloxy-17-(cyclopropylmethyl)-6,7-dehydro-4,5α-epoxy-3-hydroxy-1'-allyl-6,7-2',3'-indolomorphinan hydrochloride;
17-(cyclopropylmethyl)-6,7-dehydro-4,5α-epoxy-3-hydroxy-14-allyloxy-6,7,2',3'-indolomorphinan hydrochloride;
17-(cyclopropylmethyl)-6,7-dehydro-4,5α-epoxy-3-hydroxy-14-benzyloxy-6,7,2',3'-benzo[b]furanomorphinan hydrochloride;
17-(cyclopropylmethyl)-6,7-dehydro-4,5α-epoxy-3-hydroxy-14-allyloxy-6,7,2',3'-benzo[b]foranomorphinan hydrochloride; and
17-(cyclopropylmethyl)-6,7-dehydro-4,5α-epoxy-3-hydroxy-14-crotyloxy-6,7,2',3'-benzo[b]furanomorphinan hydrochloride.

5. A compound according to claim 4, wherein said compound is 17-(cyclopropylmethyl)-6,7-dehydro-4,5α-14-hydroxy-3-(methoxymethoxy)-6,7-2',3'-benzo [b] furanomorphinan.

6. A compound according to claim 4, wherein said compound is 17-(cyclopropylmethyl)-6,7-dehydro-4,5α-epoxy-14-hydroxy-3-(methoxymethoxy)-6,7-2',3'-(N-methoxymethylindolo)morphinan.

7. A compound according to claim 4, wherein said compound is 17-(cyclopropylmethyl)-6,7-dehydro-14-(2',6'-dichlorobenzyloxy)-4,5α-epoxy-3-(methoxymethoxy)-6,7-2',3'-benzo[b]furanomorphinan.

8. A compound according to claim 4, wherein said compound is 17-(cyclopropylmethyl)-6,7-dehydro-14-(2',6'-dichlorbenzyloxy)-4,5α-epoxy-3-hydroxy-6,7-2',3'-benzo[b]furanomorphinan.

9. A compound according to claim 4, wherein said compound is 17-(cyclopropylmethyl)-6,7-dehydro-4,5α-epoxy-3-(methoxymethoxy)-14-(3'-nitrobenzyloxy)-6,7-2',3'-benzo[b]furanomorphinan.

10. A compound according to claim 4, wherein said compound is 17-(cyclopropylmethyl)-6,7-dehydro-4,5α-epoxy-3-hydroxy-14-(3'-nitrobenzyloxy)-6,7-2',3'-benzo[b] furanomorphinan hydrochloride.

11. A compound according to claim 4, wherein said compound is 17-(cyclopropylmethyl)-6,7-dehydro-4,5α-epoxy-3-(methoxymethoxy)-14-(2-naphthylmethoxy)-6,7-2',3'-benzo[b]furanomorphinan.

12. A compound according to claim 4, wherein said compound is 17-(cyclopropylmethyl)-6,7-dehydro-4,5α-epoxy-3-hydroxy-14-(2'-naphthylmethoxy)-6,7-2',3'-benzo [b]furanomorphinan hydrochloride.

13. A compound according to claim 4, wherein said compound is 17-(cyclopropylmethyl)-6,7-dehydro-4,5α-epoxy-14-(2'-fluorobenzyloxy)-3-(methoxymethoxy)-6,7-2',3'-benzo[b]furanomorphinan.

14. A compound according to claim 4, wherein said compound is 17-(cyclopropylmethyl)-6,7-dehydro-4,5α-epoxy-14-(2'-fluorobenzyloxy)-3-hydroxy-6,7-2'-3'-benzo [b]furanomorphinan hydrochloride.

15. A compound according to claim 4, wherein said compound is 14-(cinnamyloxy)-17-(cyclopropylmethyl)-6, 7-dehydro-4,5α-epoxy3-(methoxymethoxy)-6,7-2',3'-benzo[b]furanomorphinan.

16. A compound according to claim 4, wherein said compound is 14-(cinnamyloxy)-17-(cyclopropylmethyl)-6,7-dehydro-4,5α-epoxy-3-hydroxy-6,7-2',3'-benzo[b]furanomorphinan salicylate.

17. A compound according to claim 14, wherein said compound is 17-(cyclopropylmethyl)-6,7-dehydro-4,5α-epoxy-14-methoxy-3-(methoxymethoxy)-6,7-2',3'-benzo[b]furanomorphinan.

18. A compound according to claim 14, wherein said compound is 17-(cyclopropylmethyl)-6,7-dehydro-4,5α-epoxy-3-hydroxy-14-methoxy-6,7-2',3'-benzo[b] furanomorphinan hydrochloride.

19. A compound according to claim 4, wherein said compound is 17-(cyclopropylmethyl)-14-(2'-chlorobenzyloxy)-6,7-dehydro-4,5α-epoxy-3-(methoxymethoxy)-6,7-2',3'-(N-methoxymethylindolo)morphinan.

20. A compound according to claim 4, wherein said compound is 17-(cyclopropylmethyl)-14-(2'-chlorobenzyloxy)-6,7-dehydro-4,5α-epoxy-3-hydroxy-6,7-2',3'-indolomorphinan hydrochloride.

21. A compound according to claim 4, wherein said compound is 17-(cyclopropylmethyl)-6,7-dehydro-3,14-dimethoxy-4,5α-epoxy-6,7-2',3'-benzo[b]furanomorphinan.

22. A compound according to claim 4, wherein said compound is 17-(cyclopropylmethyl)-6,7-dehydro-4,5α-epoxy-3-hydroxy-14-(3'-chlorobenzyloxy)-6,7-2',3'-benzo[b]furanomorphinan hydrochloride.

23. A compound according to claim 4, wherein said compound is 17-(cyclopropylmethyl)-6,7-dehydro-4,5α-epoxy-3-hydroxy-14-(2'-chlorobenzyloxy)-6,7-2',3'-benzo[b]furanomorphinan hydrochloride.

24. A compound according to claim 4, wherein said compound is 14-allyloxy-17-(cyclopropylmethyl)-6,7-dehydro-4,5α-epoxy-3-hydroxy-1'-allyl-6,7-2',3'-indolomorphinan hydrochloride.

25. A compound according to claim 4, wherein said compound is 17-(cyclopropylmethyl)-6,7-dehydro-4,5α-epoxy-3-hydroxy-14-allyloxy-6,7,2',3'-indolomorphinanhydrochloride.

26. A compound according to claim 4, wherein said compound is 17-(cyclopropylmethyl)-6,7-dehydro-4,5α-epoxy-3-hydroxy-14-benzyloxy-6,7,2',3'-benzo[b]foranomorphinan hydrochloride.

27. A compound according to claim 4, wherein said compound is 17-(cyclopropylmethyl)-6,7-dehydro-4,5α-epoxy-3-hydroxy-14-allyloxy-6,7,2',3'-benzo[b]furanomorphinan hydrochloride.

28. A compound according to claim 4, wherein said compound is 17-(cyclopropylmethyl)-6,7-dehydro-4,5α-epoxy-3-hydroxy-14-crotyloxy-6,7,2',3'-benzo[b] foranomorphinan hydrochloride.

* * * * *